(12) United States Patent
Knütter et al.

(10) Patent No.: US 9,772,331 B2
(45) Date of Patent: Sep. 26, 2017

(54) METHOD AND SYSTEM FOR DISEASE DIAGNOSIS VIA SIMULTANEOUS DETECTION OF ANTIBODIES BOUND TO SYNTHETIC AND CELLULAR SUBSTRATES

(75) Inventors: Ilka Knütter, Lübben (DE); Boris Radau, Berlin (DE); Dirk Roggenbuck, Strausberg (DE)

(73) Assignee: MEDIPAN GMBH, Dahlewitz/Berlin ( * ) Notice: Subject to any disclaimer, the term of this patent is extended or adjusted under 35 U.S.C. 154(b) by 294 days.

(21) Appl. No.: 13/576,888

(22) PCT Filed: Feb. 22, 2011

(86) PCT No.: PCT/EP2011/052593
§ 371 (c)(1),
(2), (4) Date: Aug. 2, 2012

(87) PCT Pub. No.: WO2011/101487
PCT Pub. Date: Aug. 25, 2011

(65) Prior Publication Data
US 2012/0308996 A1    Dec. 6, 2012

(30) Foreign Application Priority Data
Feb. 22, 2010  (EP) ..................................... 10075079

(51) Int. Cl.
*A61K 38/00* (2006.01)
*G01N 33/564* (2006.01)
*G01N 33/554* (2006.01)
*G01N 33/569* (2006.01)
*G01N 33/50* (2006.01)

(52) U.S. Cl.
CPC ......... *G01N 33/554* (2013.01); *G01N 33/564* (2013.01); *G01N 33/56972* (2013.01); *A61K 38/00* (2013.01); *G01N 33/5008* (2013.01); *G01N 2800/00* (2013.01)

(58) Field of Classification Search
None
See application file for complete search history.

(56) References Cited

U.S. PATENT DOCUMENTS 5,039,487 A    8/1991  Smith
5,912,176 A *  6/1999  Wang .............................. 435/452

FOREIGN PATENT DOCUMENTS

WO    WO 97/06440       2/1997
WO    WO2009/062479 A2  5/2009

OTHER PUBLICATIONS

Wong et al., Antineutrophil cytoplasmic antibodies in Wegener's granulomatosis, 1998, Arch Dis Child, vol. 79, pp. 246-250.*
Reiners et al., Selective killing of B-cell hybridomas targeting proteinase 3, Wegener's autoantigen, 2004, Immunology, vol. 112, pp. 228-236.*
Hayashi et al., Detection of Antinuclear Antibodies by Use of an Enzyme Immunoassay with Nuclear HEp-2 Cell Extract and Recombinant Antigens: Comparison with Immunofluorescence Assay in 307 Patients, 2001, Clinical Chemistry, vol. 47, No. 9, pp. 1649-1659.*
GE Life Sciences, Product specification FluoroLink-Ab Cy5 labelling kit PA 35000 Reagent kit for the conjugation of proteins with CyTM5 reactive dye, 2000.*
Nifli et al., Comparison of a multiplex, bead-based fluorescent assay and immunofluorescence methods for the detection of ANA and ANCA autoantibodies in human serum, 2006, Journal of Immunological Methods, vol. 311, pp. 189-197.*
Tan EM, Adv. Immunology 1982;33:167-240.
Costes SV, et al., Radiat Res. 2006;165(5):505-15.
Sack U, et al., Ann N Y Acad Sci 2009;1173:166-73.
Conrad K, et al., Ann N Y Acad Sci 2009;1173:180-185.
Hou YN, et al., Radiat Res. 2009;171(3):360-7.
Hiemann R, et al., Ann N Y Acad Sci 2007;1109:358-71.
Böcker W, et al., Radiat Res. 2006;165(1):113-24.
Hiemann R, et al., Autoimmun Rev. 2009;9:17-22.
Avaniss-Aghajani E, et al., Clin Vaccine Immunol. 2007;14:505-9.
Lal G, et al., J Immunol Methods 2005;296:135-47.
Binder SR et al, Clinical and Diagnostic Laboratory Immunology, Dec. 2005, 1353-1357.
Großmann K, et al., Cytometry A. Feb. 2011;79(2):118-25.
Hayashi N, et al, 2001, Clinical Chemistry, 47:9 1649-1659.
Smith J, et al, 2005, Ann. N.Y. Acad. Sci. 1050: 286-294.
Nifli AP, et al, Journal of Immunological methods 311 (2006), 189-197.
Bosch X, et al., Lancet 2006;368:404-18.
Van der Woude FJ, et al., Lancet 1985;1:425-9.
Csernok E, et al., Nat Clin Pract Rheumatol. Apr. 2006;2(4):174-5.
Cohen Tervaert JW, et al., Arch Intern Med 1989;149: 2461-5.
Savige J, et al., Am J Clin Path 2003;120:312-8.
Arbuckle MR et al. New Engl J Med 2003;349:1226-33.
Bradwell AR and Hughes RG. Atlas of HEp-2 patterns. 3rd ed. 2007.
Dalakas MC et al. Lancet 2003, 362:971-82.
Fox RI. Lancet 2005;366:321-31.
Rahman A et al. New Engl J Med 2008;358:929-39.
Tan EM et al. Arthritis Rheum 1997;40:1601-11.
Ziswiler H-R et al. Swiss Med Wkly 2007;137:586-90.

* cited by examiner

*Primary Examiner* — Benjamin P Blumel
(74) *Attorney, Agent, or Firm* — Law firm of Ursula B. Day

(57) ABSTRACT

The invention relates to a method and system for disease diagnosis that simultaneously detects antibodies bound to cellular and/or tissue substrates and antibodies bound to synthetic substrates, such as microparticles or beads coated with specific antigens, thereby providing a "one-step" method for the simultaneous detection and characterization of disease-associated antibodies at both low (cellular and/or tissue) and high (antigen) specificity.

17 Claims, 2 Drawing Sheets

METHOD AND SYSTEM FOR DISEASE DIAGNOSIS VIA SIMULTANEOUS DETECTION OF ANTIBODIES BOUND TO SYNTHETIC AND CELLULAR SUBSTRATES

CROSS-REFERENCES TO RELATED APPLICATIONS

This application is the U.S. National Stage of International Application No. PCT/EP2011/052593, filed Feb. 22, 2011, which designated the United States and has been published as International Publication No. WO 2011/101487 and which claims the priority of German Patent Application, Serial No. 10075079.3, filed Feb. 22, 2010 pursuant to 35 U.S.C. 119(a)-(d) the description of which is hereby incorporated by reference.

The invention relates to a method and system for disease diagnosis that simultaneously detects antibodies bound to cellular and/or tissue substrates and antibodies bound to synthetic substrates, such as microparticles or beads coated with specific antigens, thereby providing a "one-step" method for the simultaneous detection and characterization of disease-associated antibodies at both low (cellular and/or tissue) and high (antigen) specificity.

BACKGROUND OF THE INVENTION

The detection of antibodies by indirect immunofluorescence (IIF) employing different cellular and tissue substrates as multiple antigen sources has been established in routine diagnostics. Cell-based immunofluorescence tests, such as the detection of anti-nuclear antibodies (ANA) using HEp-2-cells, are widely used in clinical diagnostics and research as the industry standard (Tan E M, Adv. Immunology 1982; 33:167-240, Costes S V, et al., Radiat Res. 2006; 165(5): 505-15, Sack U, et al., Ann N Y Acad Sci 2009; 1173:166-73, Conrad K, et al., Ann N Y Acad Sci 2009; 1173:180-185). Methods for diagnosing autoimmune diseases that use indirect immunofluorescence-based approaches are known in the art. WO 97/06440 discloses a method whereby rheumatoid arthritis is diagnosed by the presence of antibodies that are directed against microtubule organising centres, or microtubules extending therefrom, in a body fluid sample of a patient. The cell line used as substrate is preferably an IT-1 macrophage cell line, which is used as a substrate to which autoantibodies present in the patient sample bind.

The increasing demand for automated reading and interpretation of fluorescence patterns, resulting in improved standardization and cost-effectiveness, has been enabled by sophisticated pattern recognition software and fully automated reading machines that are available at the present time (Hou Y N, et al., Radiat Res. 2009; 171(3):360-7, Hiemann R, et al., Ann N Y Acad Sci 2007; 1109:358-71, Böcker W, et al., Radiat Res. 2006; 165(1):113-24. Hiemann R, et al., Autoimmun Rev. 2009; 9:17-22). Indirect immunofluorescence has additionally been applied in quantitative and semi-quantitative approaches to determining antibody titre, for example in the diagnosis of diseases characterised by the presence and/or quantity of autoantibodies (WO 2009/062479 A2).

However, advances in assay development and recombinant technology have paved the way for the detection of autoantibody specificities to individual antigenic targets thereby improving the diagnostic power of antibody testing. The growing variety of antibodies found in different disorders such as infectious and rheumatic diseases has generated the need for innovative techniques, which overcome the drawbacks of single antibody detection and decrease cost and time in reporting results. Hence, multiplexed platforms have been developed recently to meet the demand of simultaneous determination of several antibody specificities in one sample. Multiplex assays based on fluorescent bead-based flow cytometry and microarray systems have proven to be powerful tools supporting higher throughput analysis and more comprehensive testing of patient samples (Avaniss-Aghajani E, et al., Clin Vaccine Immunol. 2007; 14:505-9, Lal G, et al., J Immunol Methods 2005; 296:135-47). Computer-assisted pattern recognition has also been used to analyse antigen arrays, so that antibodies that bind to a panel of disease associated antigens can be detected and correlated with a particular disease diagnosis (Binder S R et al, Clinical and Diagnostic Laboratory Immunology, December 2005, 1353-1357). Furthermore for the assessment of rheumatic-disease-specific antibodies. multiplex detection by immobilized fluorescence-coded microbeads using multicolor fluorescence can be used. This multicolor fluorescence analyses with pattern detection algorithms provide a common platform technique for the screening of ANA (Großmann K, et al., Cytometry A. 2011 February; 79(2): 118-25).

As an example, disease-specific autoantibodies (AAB) are a serological phenomenon of systemic rheumatic conditions and autoimmune liver disorders. In particular, the detection of ANA by IIF was one of the first techniques available in routine laboratories for the serological diagnosis of systemic rheumatic diseases. Despite the development of enzyme-linked immunosorbent assay (ELISA) and multiplexing technologies for the detection of disease-specific AAB, the screening for ANA by IIF assays still remains the standard method in the current multistage diagnostic approach. Recombinant or purified antigens can be provided on beads, which are subsequently analysed for antibodies that bind specifically to the selected antigens using enzyme immunoassays. Such approaches exhibit however significant disadvantages, due to severely differing sensitivities and specificities between different antigens (Hayashi N, et al, 2001, Clinical Chemistry, 47:9 1649-1659). Multiplex bead-based fluorescent assays have been published that show reasonable correlation with cell-based autoantibody diagnostic methods (Smith J, et al, 2005, Ann. N.Y. Acad. Sci. 1050: 286-294), although the low sensitivity for identifying IIF-positive control samples indicates that IIF approaches are still the favoured method (Nifli A P, et al, Journal of Immunological methods 311 (2006), 189-197).

Several substrates have been proposed for ANA IIF assays, however the screening for non-organ specific AAB on HEp-2 cells is the most established method. In general, assessment of ANA is followed by detection of specific AAB to for example extractable nuclear (ENA) and cytoplasmic antigens by immunoassays employing purified native or recombinant antigens. This two-stage approach exhibits the following benefits: (i) highly sensitive screening of the most frequent, clinically relevant non-organ specific AAB, (ii) optimal combination with other assay techniques for the down-stream differentiation of AAB reactivities based on the IIF pattern detected and the diagnosis suspected (e.g., SS-A/Ro and SS-B/La), (iii) assessment of clinically relevant AAB without the need for further testing (e.g., anti-centromere AAB), and (iv) evaluation of AAB only detectable by IIF in case of unknown autoantigenic targets or unavailable commercial assays.

Another example is the detection of anti-neutrophil cytoplasmic antibodies (ANCA) for the differential diagnosis of systemic vasculitides (Bosch X, et al., Lancet 2006; 368: 404-18). Due to the occurrence of ANCA in these systemic autoimmune disorders the term ANCA-associated vasculitis (AASV) has been coined for these clinical entities. ANCA were discovered by IIF, which is still the recommended method to detect these antibody reactivities. ANCA exhibit typically two different staining patterns of fixed granulocytes in IIF; a speckled cytoplasmic pattern (cANCA) and a perinuclear pattern (pANCA). cANCA, frequently found in patients with Wegener's granulomatosis (WG), are directed primarily against proteinase 3 (PR3), in addition to other targets, while pANCA, occurring mainly in microscopic polyangiitis (MPA), are directed primarily against myeloperoxidase (MPO) (Van der Woude F J, et al., Lancet 1985; 1:425-9; Csernok E, et al., Nat Clin Pract Rheumatol. 2006 April; 2(4):174-5), in addition to other targets.

Estimations of antibody concentrations have been proposed to be helpful in the diagnosis and management of these clinical entities. Antibody values are usually associated with the severity of disease (Cohen Tervaert J W, et al., Arch Intern Med 1989; 149: 2461-5). However, there have been other target antigens for ANCA described in IIF that can be found in patients with non-AASV (Savige J, et al, Best. Pract. Res. Clin. Rheumatol. 19: 263-76, Savige J, et al., Am J Clin Path 2003; 120:312-8). Consequently, in accordance with recently established consensus guidelines a different technique in addition to IIF for the detection of ANCA such as ELISA is recommended.

However, the techniques employed for determining several antibodies by the two- or multi-stage approach mentioned above involve a plurality of constituent tests which are individually labelled. Regarding cost-effective serological diagnostics there is a clear demand to combine the detection of antibodies to cellular and tissue antigenic targets on the one hand, and to the purified and characterised proteins thereof on the other hand, into a single method with one label.

Contemporary protein characterisation by microarray technology does not alone provide a satisfactory solution. As the number of antigenic targets to be tested on a single microarray increases, the demand for associated manufacturing equipment, miniaturization and specialized materials and handling will render the production of such microarrays increasingly complex and cost-intensive. Other techniques, including enzyme-linked immunosorbent assay (ELISA), radioimmunoassay (RIA), chromogenic assays, high-performance liquid chromatography (HPLC), gas chromatography-mass spectroscopy (GC-MS), and thin layer chromatography (TLC), exhibit the disadvantage of being limited in the number of analytes in antigenic form that can be assessed simultaneously. They are also time-consuming and require expensive equipment. In contrast, employing a HEp-2 cell substrate for ANA detection provides more than 1200 antigenic targets for antibody identification.

SUMMARY OF THE INVENTION

In light of the prior art the technical problem underlying the present invention is to provide a method for disease diagnosis, which reduces a multi-step diagnosis into a one-step procedure. This problem is solved by the features of the independent claims. Preferred embodiments of the present invention are provided by the dependent claims.

The object of the invention is therefore to provide a method and system for disease diagnosis that detects antibodies bound to cellular and/or tissue substrates and simultaneously detects antibodies bound to synthetic substrates, such as microparticles coated with specific purified native and/or recombinant antigens, thereby providing a "one-step" method for the simultaneous detection of antibodies associated with disease at both low (cellular- or tissue-specific) and high (antigen-specific) specificity.

The invention further relates to a device and kit for carrying out the method of the present invention. The method is also suited for a screening method, whereby multiple patient sera can be tested for reactivity towards any given number of specific antigens.

Therefore, an object of the invention is to provide a method for disease diagnosis comprising simultaneous detection of antibodies bound to one or more cellular substrates and one or more synthetic substrates, characterized by:
  a) providing a mixture of cellular and synthetic substrates,
  b) incubation of said substrate mixture with sample that contains the antibody to be detected,
  c) detection and/or identification of cellular and synthetic substrates and antibodies bound to said substrates using fluorescent microscopy, and
  d) evaluation of immunofluorescence image data, preferably using an automated pattern recognition interpretation system.

The cellular substrate represents a biological substrate for antigen binding, such as a mammalian cell, whereby combinations of different tissue types or cells can be applied. Tissue substrates, comprising of multiple cells of a similar type obtained from organic tissue, can also be used as the "cellular substrate" in the method of the present invention.

In a preferred embodiment of the above-mentioned method the cellular or tissue substrate can be HEp-2 cells, human granulocytes and/or organic tissue, preferably pancreatic tissue.

In a preferred embodiment the synthetic substrate is a microparticle or bead coated with purified native antigen and/or recombinant antigen. Antigens can be proteins, peptides, nucleic acids, such as DNA, multi-molecular cellular structures such as centromeres, protein complexes or protein-membrane structures, or essentially any other cellular component to which antibodies may bind. The synthetic substrate is intended to act as a carrier for a specific, or a mixture of specific, purified and/or recombinant antigens. Microparticles and bead carriers of various substances and materials are known in the art which are suitable for the method of the present invention, for example microparticles, particles or beads composed of natural or artificial polymers, sepharose, cellulose, glass or metal oxides.

In a preferred embodiment of the invention the method of disease diagnosis is characterised in that the antigen coating of the synthetic substrate is bound by antibodies associated with presence of disease. The antigen coating the synthetic substrate is selected according to its association with a known disease. The identification of antibodies binding to specific antigens therefore allows a diagnosis of disease with "high specificity", in addition to a "low specificity" detection of antibodies bound to cellular and/or tissue substrates.

The substrates of the present invention are intended to be detected and/or identified by one or more distinguishing features or parameters. In one embodiment the method of the present invention is characterised in that the optical, fluorescent, and/or physical characteristics of the substrates are used to detect and/or identify said substrates. For example the various substrates can be identified by their size, shape, fluorescent properties or other parameters during microscopic analysis. The various parameters can also be combined for the various substrates, thus representing a kind of code for substrate, antigen and/or antibody identification.

In one embodiment of the invention the method is characterised in that the fluorescent characteristic of fluorophore concentration, for example Rhodamine concentration, and/or the physical characteristic of size is used to identify the synthetic substrate, whereby the bead or microparticle size is preferably between 1-100 µm, for example 1, 2, 3, 4, 5, 10, 20, 30, 40, 50, 60, 70, 80, 90, 95, or 100 µm, or any similar value. Multiple beads or microparticles of different sizes can be combined, whereby each size of bead is coated with a different antigen, so that an array-like approach for multiple antigens can be applied simultaneously with cellular substrates.

In a preferred embodiment of the present invention multi-colour fluorescence microscopy is used to identify said substrates and/or bound autoantibodies, whereby substrates and/or bound antibodies exhibit different fluorescent colours, preferably blue, green and red.

In one embodiment of the present invention the cellular substrate is labelled with a fluorescent dye with blue emission, for example DAPI, the synthetic substrate is labelled with a fluorescent dye with green emission, for example Rhodamine or FITC, and/or the specifically bound antibody is detected by an anti-human immunoglobulin-specific antibody labeled with a fluorescent dye with red emission, for example Cy5 and/or allophycocyanin (APC).

The method of the present invention relates especially to diseases or disorders wherein antibody detection provides an effective diagnosis. In a preferred embodiment the method is characterised in that the disease is an autoimmune or infectious disorder, preferably a systemic rheumatic condition, autoimmune liver disorder, Type-1 diabetes, Lyme's disease or herpes simplex virus.

Although autoimmune diseases are difficult to diagnose, the identification of one or more specific antigens to which autoantibodies bind, in addition to the binding pattern of autoantibodies on the cellular substrate, enables a more precise diagnosis in a shorter time than what was known before. The present invention enables a method of diagnosis that combines array and cellular based approaches which was until now never considered possible.

In one embodiment of the invention the antibodies to be detected are anti-nuclear antibodies (ANA) or anti-neutrophil cytoplasmic antibodies (ANCA).

In a further embodiment of the present invention the method is characterised in that HEp-2 cells are used to analyse staining of anti-nuclear antibodies (ANA).

In a further embodiment of the present invention the method is characterised in that the ANA cellular staining patterns, the corresponding antigens and the associated diseases as presented in Table 3, Table 4 and/or Table 5 are used in disease diagnosis.

In a further embodiment of the present invention the method is characterised in that human granulocytes are used to analyse staining of anti-neutrophil cytoplasmic antibodies (ANCA).

In a further embodiment of the present invention the method is characterised in that the ANCA cellular staining patterns, the corresponding antigens and the associated diseases as presented in Table 1 and/or Table 2 are used in disease diagnosis.

In a further embodiment of the present invention the method is characterised in that the anti-neutrophil cytoplasmic antibodies (ANCA) exhibit a perinuclear staining (p-ANCA) or speckled cytoplasmic staining (cANCA) of human granulocytes.

In a further embodiment of the present invention the method is characterised in that the antibodies are targeted against the Proteinase 3 (PR3) or myeloperoxidase (MPO) proteins, or antigens thereof.

In a further embodiment of the present invention the method is characterised in that the antibodies exhibit speckled cytoplasmic staining (cANCA) of human granulocytes and bind Proteinase 3 (PR3), whereby the protein or antigens thereof are provided on a synthetic substrate, therefore providing a diagnosis of Wegener's granulomatosis (WG).

In a further embodiment of the present invention the method is characterised in that the antibodies exhibit perinuclear staining (p-ANCA) of human granulocytes and bind myeloperoxidase (MPO), whereby the protein or antigens thereof are provided on a synthetic substrate, therefore providing a diagnosis of ANCA-associated vasculitis (AASV).

In a further embodiment of the present invention the method is characterised in that the sample comprises blood, serum, cerebrospinal fluid, synovial fluid, or saliva obtained from a subject, whereby the subject is to be understood as a patient suspected to have a disease or illness that is to be diagnosed using the method of the present invention.

The invention also encompasses a method whereby the interpretation system is controlled by specially designed software, such as software that has been developed specifically for application in the method of the present invention, consisting of modules for devices and autofocus control, image acquisition, image analysis, and/or pattern recognition algorithms.

In one embodiment the method of the invention is characterised in that the interpretation system is used to evaluate the immunofluorescence image data according to the following hierarchy:
  i) positive staining signal,
  ii) localization of staining, preferably by classification of staining patterns into cellular substrate or synthetic substrate, and
  iii) determination of cellular patterns, preferably perinuclear and/or cytoplasmic patterns for granulocytes; nuclear, cytoplasmic and/or chromatin of mitotic cells patterns for HEp-2 cells.

This hierarchy facilitates a fast and accurate analysis of the acquired microscopic images, therefore allowing a diagnosis on the basis of multiple parameters within the immunofluorescent data.

In one embodiment the method of the invention is characterised in that classification of staining patterns into cellular or synthetic and the determination of cellular patterns is achieved through a combination of structure and texture characteristics of the immunofluorescence image by defining a set of rules for each pattern. This classification can be carried out by specially designed software, such as software that has been developed specifically for application in the method of the present invention.

A further aspect of the invention relates to a system for the simultaneous detection of antibodies bound to one or more cellular substrates and one or more synthetic substrates according to the method of any one of the preceding claims, comprising
  a) a fluorescent microscope with a camera, a motorized scanning stage and multichannel light-emitting diodes (LED), and
  b) a computing device with software consisting of modules for devices and autofocus control, automated image acquisition, automated image analysis, and automated pattern recognition algorithms whereby three colour channels are analysed, preferably blue, green and red.

The system of the present invention has been developed specifically for application in the method of disease diagnosis of the present invention. Such a system can comprise of a fluorescent microscope coupled to a data processing computer, such as a PC.

An aspect of the invention is also a kit for the simultaneous detection and or identification of antibodies bound to one or more cellular substrates and one or more synthetic substrates according to the method of claims 1-21, comprising a) slides with fixed cellular substrate mixed with the antigen-coated synthetic substrate, whereby the cellular substrate is preferably HEp-2 cells and/or human granulocytes, and the synthetic substrates are distinguished from one another according to their optical, fluorescent, and/or physical characteristics, and b) conjugate with immunoglobulin-specific antibody conjugated with a fluorescent label, preferably FITC, Cy5 and/or APC, and optionally wash buffer, cover slips, covering medium, uncoated synthetic substrate, either with or without fluorescent label, and/or additional fluorescent labels for synthetic substrates.

The kits of the present invention enable an extremely simplified and economic method of diagnosis compared to the standards known in the art. A kit slide can contain multiple synthetic substrates with multiple epitopes, essentially combining an array based approach with the cellular substrate approach, therefore providing a more complete and efficient diagnostic tool than anything known in the art, which is present in a compact form that is economically viable.

DETAILED DESCRIPTION OF PREFERRED EMBODIMENTS

The method of the present invention enables the diagnosis of diseases for which multi-step diagnostics are usually required. The multiple diagnostic steps of evaluating antibody binding at increasing specificities are combined within this method to provide a faster, more efficient and exact diagnosis in a single diagnostic analysis.

This method relates especially to diseases or disorders wherein antibody detection provides an effective diagnosis, such as infectious diseases and autoimmune disorders. The method allows screening of not only the presence and pattern of antibody binding on cells or tissues, but can also provide more specific information on the individual antigens to which the antibodies are directed. This facilitates the diagnosis of specific disorders in a one-step method.

The term diagnosis refers to the identification and/or determination of the nature or cause of a disease through evaluation of patient characteristics. The present invention provides a diagnostic method that when carried out provides an indication of a particular disease or diseases that may be present in the patient. For example, multiple autoimmune diseases may be present in any one subject, so that the method of the present invention does not exclude the existence of other diseases by the identification of one disease, for example multiple diseases could also be either simultaneously or separately detected, or diagnosed, using the method of the present invention.

The method of the present invention is particularly suited for the diagnosis of systemic rheumatic inflammatory disorders, such as autoimmune systemic vasculitides. Such disorders associated with antibodies directed against antigens within granulocytes (ANCA), such as microscopic polyangiitis (MPA), associated with antibodies against Myeloperoxidase (MPO), and Wegener's granulomatosis (WG), associated with antibodies against Proteinase 3 (PR3), can de diagnosed using the method of the present invention. Systemic lupus erythematosus can be diagnosed, for example when associated with antibodies directed double-stranded DNA. Polymyositis can also be diagnosed using the present invention, for example when associated with antibodies directed against antigens within HEp-2 cells, such as tRNA synthetases.

Autoimmune liver disorders can also be diagnosed with the present invention, such as autoimmune hepatitis, for example when associated with antibodies directed against antigens within HEp-2 cells. Disorders associated with antibodies against fibrillic actin, the asialoglycoprotein receptor or other antigens within hepatocytes can also be diagnosed.

Presented in Table 1 is a list of relevant anti-neutrophil cytoplasmic antibody types and associated cellular patterns in granulocytes. Table 1 provides examples of antibodies, staining patterns and their associated clinical relevance. This table is not intended to limit the scope of the invention.

TABLE 1

Antibody types and relevant cellular patterns

| Antibody | Antigen, Epitope | Histological Distribution | IFT-detection and other methods | Occurrence and diagnostic relevance |
| --- | --- | --- | --- | --- |
| ANCA | Enzymes in cytoplasmic granula, neutrophil granulocytes, eg. Proteinase 3, Myeloperoxidase, Elastase, Cathepsin G, Azurocidin, Lactoferrin, Lysozyme, BPI | Cytoplasm: specific granula (neutrophil granulocytes) | granular, perinuclear or atypical (cytoplasmic): cANCA, pANCA, aANCA or xANCA; indirect IFT on neutrophil granulocytes (ethanol or formalin fixed) | cANCA (Proteinase 3) and pANCA (Myeloperoxidase) are markers for systemic vasculitis. In addition, typical or atypical pANCA-patterns are found in rheumatic arthritis, chronic inflammatory bowel diseases, primary sclerosing cholangitis and cystic fibrosis. |
| cANCA | Enzymes in cytoplasmic granula neutrophil granulocytes: | Cytoplasm: specific granula (neutrophil | granular (ccytoplasm), cANCA: often due to antibodies directed | cANCA (Proteinase 3) almost exclusively in Wegener's granulomatosis, |

TABLE 1-continued

Antibody types and relevant cellular patterns

| Antibody | Antigen, Epitope | Histological Distribution | IFT-detection and other methods | Occurrence and diagnostic relevance |
|---|---|---|---|---|
| | Proteinase-3 (PR-3) and BPI | granulocytes) | against PR-3, also due to antibodies directed against BPI, indirect IFT on neutrophil granulocytes (ethanol or formalin fixed) | screening also in potential cases of systemic vasculitis |
| pANCA | Enzymes in cytoplasmic granula neutrophil granulocytes: Myeloperoxidase (MPO), Elastase, Cathepsin G, Azurocidin, Lactoferrin, Lysozyme and other as yet unidentified target antigens | Cytoplasm: specific granula (neutrophil granulocytes) | perinuclear (cytoplasm), pANCA: most often due to antibodies directed against MPO. The pattern is caused by shifting during ethanol-fixing. With formalin-fixing the pattern is granular cytoplasmic; indirect IFT on neutrophil granulocytes (ethanol fixed) | pANCA is indicated in vasculitis (ANCA-associated vasculitis, eg microscopic polyangitis and pauci-immune glomerulonephritis), chronic inflammatory bowel diseases, auto-immune hepatitis |

Presented in Table 2 is a list of relevant antigens that can be applied to the synthetic substrate of the present invention. This listing is not intended to limit the scope of the invention. From Table 1 it is apparent that for each of the cellular patterns multiple diseases can be indicated. In order to provide a more concrete diagnosis, more detailed information is required on the particular antigen to which the autoantibodies bind. It becomes apparent from Table 2 that each of the particular antigens exhibits a close association with a disease, so that a positive signal for such an antigen in the method of the present invention, in combination with the cellular pattern, enables an improved diagnosis in comparison to those techniques known in the art.

The present invention therefore represents a novel combination of analytical techniques to provide an improved diagnosis. The invention relates to a combination invention, whereby the novelty of the individual components is unimportant, but rather the particular combination as claimed leads to surprising results and to a synergistic effect. The present invention exhibits a synergistic effect between the components, whereby the simultaneous analysis of patient antibodies at both low (cellular and/or tissue) and high (antigen) specificity provides a much faster method and more concrete diagnosis compared to those methods known in the prior art.

TABLE 2

Individual antigens that are relevant for application on the synthetic substrate or beads of the present invention

| Antibody | Antigen, Epitope | Histological Distribution | IFT-detection and other methods | Occurrence and diagnostic relevance |
|---|---|---|---|---|
| Myeloperoxidase | Myeloperoxidase, Homodimer of approx. 140 kD, catalyses the peroxidation of chloride to hypochloride; intracellular destruction of phagocytosed microorganisms, inactivation of protease inhibitors | Cytoplasm: azurophil granula (neutrophil granulocytes) | ELISA with purified Myeloperoxidase | MPO-ANCA is a diagnostic marker for microscopic polyangitis (MPA) and for pauci-immune, focal necrotic glomerulonephritis (can develop to a rapid-progressive glomerulonephritis, RPNG. Note: pauci-immune glomerulonephritis either as a part of systemic vasculitis or as idiopathic form (no extra-renal vasculitis) |
| Proteinase 3 | Proteinase-3, neutral serine proteinase | Cytoplasm: azurophil granula (neutrophil granulocytes) | ELISA with purified or recombinant proteinase-3 (expressed in eukaryotic cells) | PR3-ANCA is a diagnostic marker for Wegener's granulomatosis. Early and abortive forms, in addition to a number of limited Wegeners forms, can be |

TABLE 2-continued

Individual antigens that are relevant for application on the synthetic substrate or beads of the present invention

| Antibody | Antigen, Epitope | Histological Distribution | IFT-detection and other methods | Occurrence and diagnostic relevance |
|---|---|---|---|---|
| | | | | diagnosed due to the high specificity. PR3-ANCA signal is correlated with the activity of the disease |
| Elastase | Elastase | Cytoplasm: azurophil granula (neutrophil granulocytes) | ELISA with purified Elastase | cf. pANCA |
| Cathepsin G | Cathepsin G | Cytoplasm: azurophil granula (neutrophil granulocytes) | ELISA with purified Cathepsin G | cf. pANCA |
| Lactoferrin | Lactoferrin | Cytoplasm: azurophil granula (neutrophil granulocytes) | ELISA with purified Lactoferrin | cf. pANCA |
| Lysozyme | Lysozyme | Cytoplasm: azurophil granula (neutrophil granulocytes) | ELISA with purified Lysozyme | cf. pANCA |
| Azurocidin | Azurocidin, cationic anti-microbiological protein (CAP37) | Cytoplasm: azurophil granula (neutrophil granulocytes) | ELISA with purified Azurocidin | Azurocidin-ANCA predominantly in systematic vaculitis; Azurocidin antibodies can often be detected together with other ANCA-specificities |

Presented in Table 3 is a list of relevant anti-nuclear antibodies and associated clinical relevance. This listing does not limit the scope of the invention. The incidence of anti-nuclear antibodies in systemic autoimmune diseases is represented. The incidence of anti-nuclear antibodies and their association with specific diseases is known in the art (Arbuckle M R et al. New Engl J Med 2003; 349:1226-33, Bradwell A R and Hughes R G. Atlas of HEp-2 patterns. 3rd ed. 2007, Dalakas M C et al. Lancet 2003, 362:971-82, Fox R I. Lancet 2005; 366:321-31, Rahman A et al. New Engl J Med 2008; 358:929-39, Tan E M et al. Arthritis Rheum 1997; 40:1601-11, Ziswiler H-R et al. Swiss Med Wkly 2007; 137:586-90).

ABBREVIATIONS

SLE: systemic lupus erythematosus; MCTD: mixed connective tissue disease (Sharp-Syndrom); DM/PM dermato-/polymyositis; RA: rheumatoid athritis; SSc: systemic sclerosis/scleroderma; LSSC: limited systemic scleroderma (CREST-syndrome); med. LE: medicament-induced lupus erythematosus; AIC: autoimmune cholangitis; PBC: primary biliary cirrhosis.

The diseases provided in Tables 1 to 4 are intended as examples of illnesses, conditions and/or diseases that are to be diagnosed by the method of the present invention.

TABLE 3

Incidence (%) of anti-nuclear antibodies (IgG) in systemic autoimmune diseases

| Antigen Hep-2 | SLE | Med. LE | MCTD | RA | Sjögren | SSc | LSSc | DM/PM |
|---|---|---|---|---|---|---|---|---|
| ANA IIF HEp2 1: ≥160 [a] | 95 | 95 | 100 | 14 | 74 | 87 | 55-80 | 60 |
| ds-DNA | 70-80 | 3 | <5 | <5 | <5 | <5 | <5 | <5 |
| nucleosomes | 60-90 | 95 | <5 | 11 | 8 | <5 | — | <5 |
| centrosomes | — | — | — | — | — | 10 | 55-80 | — |
| Sm | 10-30 | — | — | — | — | — | — | — |
| U1-snRNP (Sm-RNP) [b] | 60 | — | 100 | <5 | 3 | 6 | <5 | 6 |
| snRNP p68/A | 20-50 | — | 100 | <5 | 3 | 6 | <5 | 6 |
| SS-A/Ro p52 | 30 [c] | — | <5 | <5 | 65 | <5 | <5 | 25 [d] |
| SS-A/Ro p60 | 30-40 | — | <5 | 10 | 75 | 9 | <5 | 15 |
| SS-B/La | 15-20 [c] | — | <5 | 15 | 50 | <5 | <5 | 5 |
| rRNP [e] | 20 | — | — | — | — | — | — | — |
| Scl-70 | — | — | — | — | 5 | 30-50 | 13 | 10 |
| fibrillarin (U3-snoRNP) | — | — | — | — | — | 8 | 3 | — |
| RNA-polymerases | <5 | — | <5 | <5 | — | 4-20 | — | — |
| Jo-1 | — | — | — | — | — | — | 3 | 16 |
| PL-7, PL-12 | — | — | — | — | — | — | — | 4 |

TABLE 3-continued

Incidence (%) of anti-nuclear antibodies (IgG) in systemic autoimmune diseases

| Antigen Hep-2 | SLE | Med. LE | MCTD | RA | Sjögren | SSc | LSSc | DM/PM |
|---|---|---|---|---|---|---|---|---|
| SRP | — | — | — | — | — | — | — | <3 |
| Mi-2 | — | — | — | — | — | — | — | 10-15 |
| PM-Scl | — | — | — | — | — | 3 | — | 8 |
|  |  |  |  |  |  | 25-50 [f] |  | 25-50 [f] |
| PCNA | 3 | — | — | — | — | — | — | — |

Legend for Table 3:
[a] Specificity 95%
[b] U1-snRNP-complex: IgG against Sm and/or U1-snRNP p68/A and/or tertiary epitopes
[c] Pathogenetic significance in neonatal lupus with av-Block in up to 5% of cases. SS-A/Ro52 IgG recognise a cardial 5-HT4 serotoninergic receptor and inhibit via serotonin activated L-type calcium streams (ICa).
[d] SS-A/Ro p52 IgG together with Jo-1 IgG in inflammatory myopathies
[e] rRNP: ribosomal RNP with the proteins P0, P1 and P2
[f] In DM/PM with SSc Table 4 presents nuclear patterns (IIF) for anti-nuclear antibodies when bound to HEp-2 cells. It can be seen from Table 4 that similar or the same cellular/nuclear patterns are visible for different diseases. Table 5 presents further cellular patterns (cytoplasmic) for antibodies bound to HEp-2 cells. Although a cellular analysis can provide evidence or support for the presence or absence of an autoimmune disease, indirect immunofluorescence using only cellular substrates cannot provide an optimal concrete diagnosis. Also provided in Tables 4 and 5 are lists of particular antigens, which could be applied to the synthetic substrate of the present invention. The combination of cellular pattern (nuclear interphase, mitoses and cytoplasm) and specific antigen (Antigen) then leads to an improved and more certain diagnosis of the illness or condition.

TABLE 4

Detection of anti-nuclear antibodies (ANA) on HEp-2 cells (ANA IIF HEp2)

| Nuclear interphase | Mitoses (Chromatin) | Antigen | Disease-association |
|---|---|---|---|
| fine speckled, | negative | SS-A (Ro52 oder Ro60), SS-B (La) | Sjögren, SLE, MCTD |
| fine speckled, | negative | RNA-Polymerase II, | SSc |
| fine speckled, | negative | Ku, inter alia | SLE, Sjögren, SSc, DM/PM |
| fine speckled, | negative | Mi-2 (Helicase) | DM-SSc |
| speckled | negative | Sm | SLE |
| speckled | negative | U1-snRNP | MCTD, SLE, SSc |
| speckled | negative | other snRNP | PM-SSc, SLE, MCTD, Raynaud, Sjögren |
| coarse speckled | negative | hnRNP (nuclear matrix) | SLE, MCTD, RA, SSc |
| speckled, 46 points/nuclear | positive | Centromere (mainly CENP-B) | LSSc |
| speckled, 5-15 points/nuclear | negative | Nuclear dots (sp100) | AIC/PBC |
| speckled, 2-6 points/nuclear | negative | Nuclear coiled bodies (p80 coilin) | AIC/PBC |
| speckled, single cells (S-Phase) | negative | PCNA (Cyclin) | SLE |
| homogenous/nucleolus circular form | weak | Scl-70 (Topoisomerase) | SSc |
| homogeneous/peripheral | positive | ds-DNA | SLE |
| homogeneous/peripheral | positive | Histone | Med. LE |
| membrane granular | negative | Nucleoporins, gp210 | AIC/PBC |
| nucleolus speckled | dotted | RNA-Polymerase I, nuclear organising regions (NOR) | SSc, SLE, MCTD, RA |
| nucleolus clumpy | positive | Fibrillarin (U3-snoRNP) | SSc |
| nucleolus homogeneous | negative | PM-Scl | DM/PM + SSc |
| nucleolus homogeneous, nucleoplasma weak homogeneous-speckled | negative | Th/To | LSSc, Raynaud, SLE, PM, RA |

TABLE 5

| Cytoplasm | Antigen | Disease-association |
|---|---|---|
| speckled, diffuse | mitochondria (pyruvatde hydrogenase) | PBC |
| granular, fine, diffuse | ribosomal P-Proteins (rRNP) | SLE |
| granular | Jo-1 (histidyl-tRNA-synthetase) | PM |
| granular | PL-7 (threonyl-tRNA-synthetase) | PM |

TABLE 5-continued

| Cytoplasm | Antigen | Disease-association |
|---|---|---|
| granular | PL-12 (alanyl-tRNA-synthetase) | PM |
| granular | SRP (54 kDa (amongst others) proteins) | Anti-SRP-myopathy-syndrome, mostly related to a PM |
| fibrillar, diffuse | polymerised actin | AIHep Type 1 |
| fibrillar, diffuse | tubulin, vimentin | Infektions |

Type 1 diabetes can also be diagnosed using the present invention, for example when associated with antibodies directed against islet cells of the pancreas, glutamate decarboxylase or tyrosine phosphatase IA-2.

A further class of disorders that can be diagnosed with the method of the present invention relate to infectious diseases. Such diseases include Borreliosis or Lymes disease, where the disease is associated with antibodies directed against Borrelia or Borrelia proteins such as p21, p41, p100, OSPC or OSPA.

Herpes Simplex virus is another infectious disease which can be diagnosed using the present invention, for example when associated with antibodies directed against herpes simplex virus Type 1 (Herpes Labialis) and type 2 (Herpes Genitalis). Herpes-infected cells can be used as the cellular substrate, together with synthetic substrate containing specific Herpes-antigens, such as gG1 and gC1 for type 1 and gG2 for type 2.

The use of antigen-coated small supports, such as microparticles coded by optic or physical characteristics thereof, or by attaching information molecules, together with cellular and/or tissue substrates in one test environment, surprisingly provides a suitable basis for the simultaneous assessment of multiple antibody activities outlined in the multi-stage approach above.

The optimal reporter method for such a detection technique is multi-colour fluorescence, which can readily be employed for both the coding of particles and as a label for the assessment of multiple specific antibody-antigen interactions simultaneously. A fully automated microscope with pattern recognition software reads the fluorescent signals that code for particles coated with various specific antigens, in addition to the fluorescence signals arising from the detection of target-bound antibodies on particles, cellular and/or tissue substrates.

The pattern recognition software enables the simultaneous determination of both cellular and/or tissue and synthetic substrates. A defined set of rules for each pattern (for both cellular/tissue and substrate patterns) allows the software to identify to which specific substrate each fluorescent signal corresponds. This occurs through the unique optical, fluorescent, and/or physical characteristics of the different substrates. These characteristics act as a code for the software to recognize to which substrate (and therefore to which specific antigen) the antibodies have bound. The automatic determination of specific cellular patterns (such as perinuclear and cytoplasmic for granulocytes; nuclear, cytoplasmic, speckled cytoplasmic, chromatin of mitotic cells for HEp-2 cells) provides additional information leading to the diagnosis of disease, as explained for MPA and WG above.

The use of sophisticated pattern recognition abolishes the need for staff to be highly trained and to understand several different system set-ups and the fluorescent patterns that are specific for particular antibodies. Such requirements usually require extensive costs in staff training. In terms of quality standards and validation specifications, it is often necessary to run experimental repetitions, requiring supervision by scientists or otherwise highly-trained staff. A consistent reproducibility and high quality is particularly required for cell based IIF. Interpretation of immunofluorescence patterns is influenced by the knowledge and individual qualification of the investigator. Thus, a high intra- and inter-laboratory variability is common and represents a major diagnostic problem, especially in non-specialized laboratories.

Automated reading of immunofluorescence patterns for the detection of antibodies to cellular and purified antigenic targets by automated interpretation systems and intelligent pattern recognition provides a reliable basis for cost-effective serological diagnostics, particularly for laboratories with large sample numbers. The opportunity to apply modern electronic data analysis and management can significantly alleviate the heavy workload in such laboratories.

DESCRIPTION OF THE FIGURES

The invention is further described by the figures. These are not intended to limit the scope of the invention.

FIG. 1: The results of the simultaneous immunofluorescent analysis of ANCA and antibodies to MPO are shown in FIG. 1. One serum sample, already having been tested as positive for pANCA (MPO), and another serum sample, already having been tested positive for cANCA (PR3), were tested on slides with human granulocytes together with MPO coated microparticles. The location of granulocytes on the slide was detected by DAPI staining whereas the antigen coated microparticles were assessed by Rhodamine or FITC fluorescence. The pANCA positive serum demonstrated a positive signal with both the immobilized granulocytes and the MPO coated microparticles. Antibody binding to MPO localized in the granulocytes and immobilized on the particles (shown with arrows) was shown by specific staining with the Cy5 conjugate. In contrast, the cANCA positive serum generated a positive reaction with the granulocytes only.

FIG. 2: The results of the simultaneous immunofluorescent analysis of ANCA and antibodies to PR3 are shown in FIG. 2. One serum sample, already having been tested as positive for pANCA (MPO), and one serum sample, already having been tested as positive for cANCA (PR3), were tested on slides with human granulocytes together with PR3 coated microparticles. The location of granulocytes was detected by DAPI staining whereas the antigen coated microparticles assessed by Rhodamine or FITC fluorescence. The cANCA positive serum demonstrated a positive signal with both the immobilized granulocytes and the PR3 coated microparticles. Antibody binding to PR3 localized in the granulocytes and immobilized on the particles (shown with arrows) was shown by specific staining with the Cy5 conjugate. In contrast the pANCA positive serum generated a positive reaction with the granulocytes only.

EXAMPLES

Figure 1:
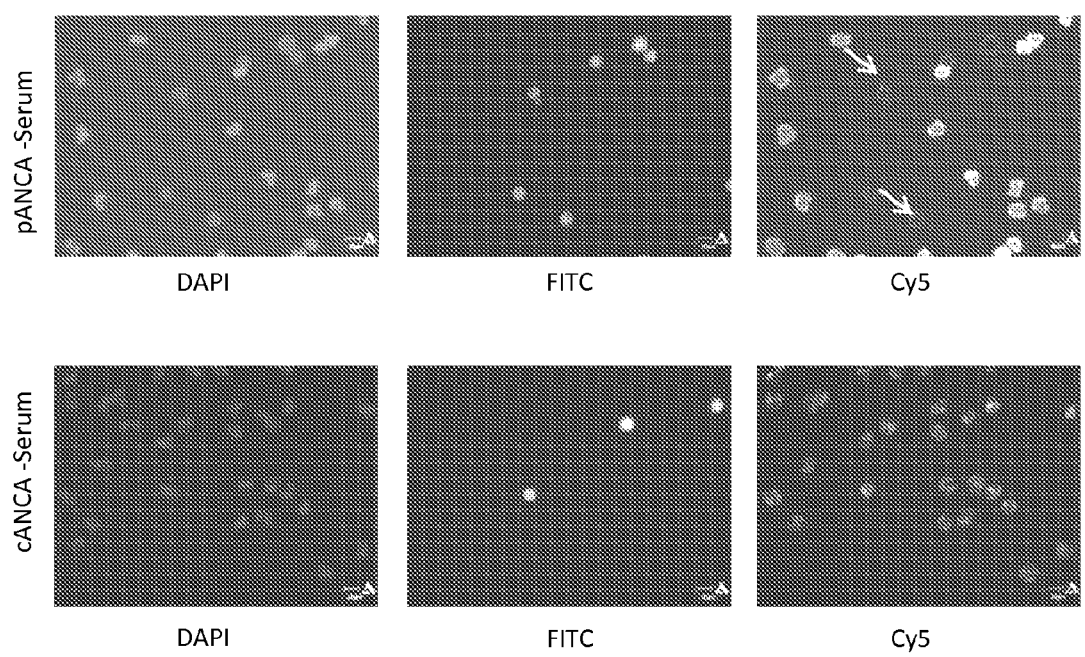
FIG. 1: Simultaneous Immunofluorescent analysis of ANCA and antibodies to MPO

The following methods are used in carrying out the present invention as demonstrated in the examples. They are intended to further describe the invention by way of practical example and do not represent a limiting description of the invention.

Patients:

Serum samples from 10 patients with WG positive for cANCA in IIF (PR3 positive) and 10 patients with other AASV positive for pANCA (MPO positive) were collected and stored at −20° C. The diagnosis of WG was based on the Chapel Hill Consensus Definitions for WG. Ten patients fulfilling the diagnostic criteria of systemic lupus erythematosus (SLE) were enrolled as disease controls in the study. Sera from 10 blood donors were used as healthy controls. All samples were taken at the time of consent and enrolment.

ANCA Detection by Conventional IIF:

ANCA were detected by running patient samples on ethanol- and formalin-fixed human granulocytes according to the recommendations of the manufacturer (GA Generic Assays GmbH, Dahlewitz, Germany). Briefly, fixed granulocytes were incubated in a moist chamber at room temperature (RT) for 30 minutes with 25 µl of serially diluted serum, starting with a dilution of 1:20. After washing, immune complexes were detected by incubating the samples with fluorescein-conjugated sheep anti-human IgG for 30 minutes at RT. Samples were subsequently washed, embedded, and manually analysed by the fluorescence microscope.

Detection of MPO and PR3 Antibodies by ELISA:

Proteinase-3 and MPO autoantibodies in the patient sera were detected using ELISA of different generations employing purified human PR3 and MPO as solid-phase antigen, respectively, according to the recommendations of the manufacturers (GA Generic Assays GmbH, Dahlewitz, Germany; Aesku.Diagnostics GmbH, Wendelsheim, Germany).

Simultaneous Detection of ANCA and Antibodies to MPO and PR3:

Human granulocytes were isolated via a density gradient. The band enriched with granulocytes was collected. After lysis of the erythrocytes, the granulocytes were washed with PBS. The separated granulocytes were mixed with Rhodamine labelled MPO or PR-3 coated beads. This mixture was immobilized onto the surface of 6-well diagnostic glass slides. The slides were fixed with ethanol. For IIF, the combined granulocytes/bead slides were incubated in a moist chamber at room temperature (RT) for 30 minutes with 25 µl of 1:20 diluted serum. After washing, bound immune complexes were detected by incubating the samples with Cy5-conjugated goat anti-human IgG antibody (Dianova, Hamburg, Germany) for 30 minutes at RT. Samples were subsequently washed, embedded, and analysed by the system for automated pattern recognition of fluorescence signals (see below).

Automated Pattern Recognition of Fluorescent Signals:

Fluorescent patterns of serum samples for simultaneous multiplex detection of antibodies bound to cellular antigens, and bound to antigens coated on microparticles, were assessed automatically employing a motorized inverse microscope (Olympus IX81, Olympus Corp., Japan) with a motorized scanning stage (IM120, Märzhäuser, Germany), 400 nm, 490 nm, 525 nm and 635 nm light-emitting diodes (LED) (precisExcite, CoolLED, UK), and a grey-scale camera (PS4, Kappa, Germany). The interpretation system is controlled by specially designed software, consisting of modules for devices and autofocus control, image analysis, and pattern recognition algorithms. The novel autofocus based on Haralick's image characterization of objects through grey-scale transition used 4',6-diamidino-2-phenylindole (DAPI) as fluorescent dye for object recognition and focusing. To eliminate artifacts, an additional qualitative image analysis was performed by dividing the image into sub-objects of equal size.

Object segmentation was conducted using a histogram-based threshold algorithm followed by watershed transformation. Segmented objects were characterized by regional, topological, and texture/surface descriptors. More than 1,400 object-describing criteria were implemented.

Immunofluorescence image data were evaluated according to the following hierarchy: i) positive staining signal, ii) localization of staining (cellular or microparticle), and iii) determination of cellular staining patterns: perinuclear, cytoplasmic).

Cells were identified by DAPI staining and microparticles by Rhodamine fluorescence. FITC fluorescence was also used for identifying the synthetic substrate. Cy5 specific immunofluorescence was analyzed in the third fluorescence channel for specific binding of antibody. Classification was achieved through combination of structure and texture characteristics by definition of rules for each object.

A reactivity index (RI) was calculated by combining absolute image intensity, contrast, and number of grey-scale levels of the total image for the assessment of image data. Since RI is influenced by exposure time, which depends on the highest image signal after exclusion of artifacts, even patterns with weak absolute signals can be detected. The determination of threshold values for the differentiation of positive signals was conducted on the basis of RI values of 200 normal blood donors.

The invention is further described by the following examples. These are not intended to limit the scope of the invention.

Example 1: Simultaneous Detection of ANCA and Antibodies to MPO

For the simultaneous detection of ANCA and antibodies to MPO, human granulocytes in suspension with MPO coated beads were immobilized in the wells of 6-well diagnostic glass slides. The nuclei of the granulocytes were detected by staining with DAPI, whereas the coated beads were localized by Rhodamine labelling. For the IIF, combined granulocyte/bead slides were incubated with 1:20 diluted serum. After washing, formed immune complexes were detected by incubating the samples with Cy5-conjugated goat anti-human IgG.

The slides with granulocytes and MPO-coated beads were analysed (FIG. 1). In the upper panel, staining images of a pANCA serum taken with the three different channels for DAPI (left side), FITC/Rhodamine (middle) and Cy5 (right side) are demonstrated. In the lower panel, the combined slide was stained with a cANCA serum. Only the image stained with the pANCA serum also showed a positive staining for MPO-coated particles in the specific Cy5 channel. Therefore, the perinuclear staining of the granulocytes, which is typical for MPO antibodies, was confirmed by the staining of the MPO-coated beads.

Example 2: Simultaneous Detection of ANCA and Antibodies to PR3

For the simultaneous detection of ANCA and antibodies to PR3, human granulocytes in suspension with PR3 coated beads were immobilized in the wells of 6-well diagnostic glass slides. The nuclei of the granulocytes were detected by staining with DAPI, whereas the coated beads were localized by Rhodamine labelling. For the IIF, combined granulocyte/bead slides were incubated with 1:20 diluted serum.

After washing, formed immune complexes were detected by incubating the samples with Cy5-conjugated goat anti-human IgG.

Figure 2:
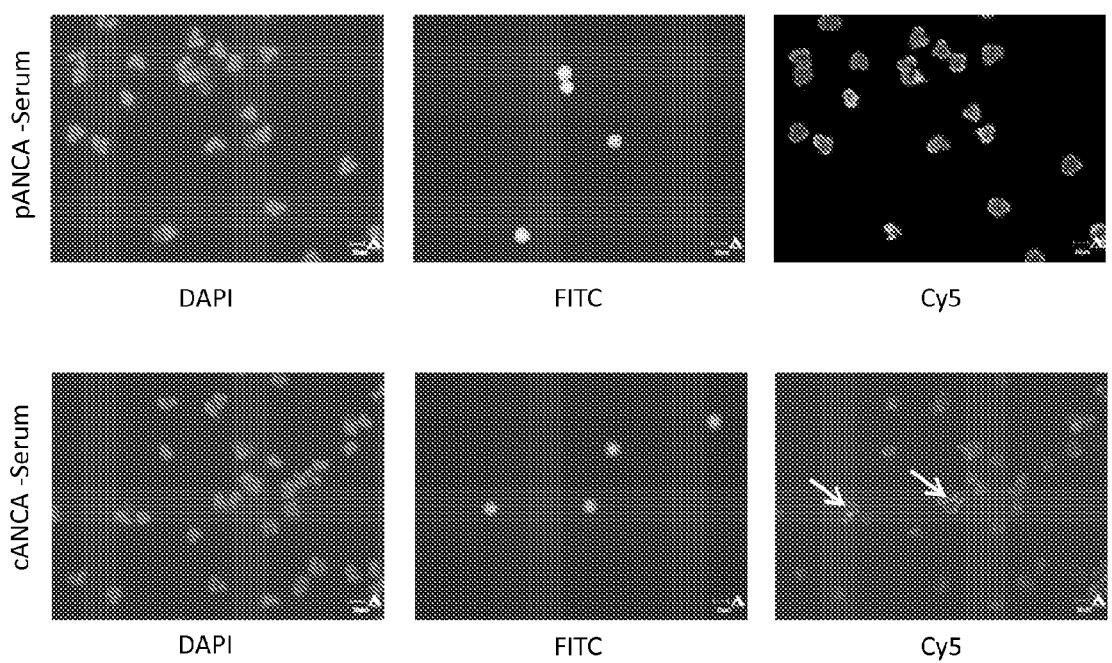
FIG. 2: Simultaneous Immunofluorescent analysis of ANCA and antibodies to PR3

The slides with granulocytes and PR3-coated beads were analysed (FIG. 2). In the upper panel, staining images of a pANCA serum taken with the three different channels for DAPI (left side), FITC/Rhodamine (middle) and Cy5 (right side) are demonstrated. In the lower panel, the combined slide was stained with a cANCA serum. FIG. 2 shows the staining images using PR3-coated microparticles, instead of MPO-coated particles as in example 1. In contrast to example 1, the cANCA serum demonstrates a positive reaction with beads coated with PR3 in the lower panel. Thus, the cytoplasmic staining of the granulocytes typical for PR3 antibodies was confirmed by the staining of the PR3 coated beads.

Example 3: Evaluation of Disease-Specific and Control Sera

In order to test the specificity of the detection of ANCA, anti-PR3 and, anti-MPO antibodies by means of IIF on slides with both granulocytes and antigen-coated microparticles, 10 anti-PR3 positive WG patient sera, 10 anti-MPO positive AASV patient sera, 10 SLE patient sera, and 10 blood donor sera were assessed. The diagnosis of WG was based on the Chapel Hill Consensus Definitions for WG. Ten patients fulfilling the diagnostic criteria of SLE were enrolled as disease controls in the study. Sera from 10 blood donors were used as healthy controls.

ANCA reactivity was determined in accordance with the immunofluorescence pattern of positive granulocyte staining. Reactivity to either MPO- or PR3-coated microparticles was evaluated simultaneously by detection of positive microparticle staining.

Almost all WG sera which were positive for cANCA in IIF revealed a positive reactivity with the PR3-coated beads (90%) and a cANCA pattern with fixed granulocytes (100%) of the combined slide. In contrast, all AASV sera which were positive for pANCA in IIF demonstrated a positive reactivity with MPO-coated beads and a pANCA pattern with fixed granulocytes. All control patients were negative either with the fixed granulocytes or the antigen-coated microparticles. The results are shown in Table 6.

Further studies using the method of the present invention to diagnose diseases associated with ANA reveal similarly effective results.

TABLE 6

Simultaneous detection of ANCA on granulocytes and antibodies to MPO and PR3 on antigen-coated beads

| | granulocytes | | microparticles | |
|---|---|---|---|---|
| | cANCA | pANCA | anti-PR3 | anti-MPO |
| anti-PR3 pos. WG patients | 10/10 | 0/10 | 9/10 | 0/10 |
| anti-MPO pos. AASV patients | 0/10 | 9/10 | 0/10 | 10/10 |
| SLE patients | 0/10 | 0/10 | 0/10 | 0/10 |
| Blood donors | 0/10 | 0/10 | 0/10 | 0/10 |

What is claimed is:

1. A method for simultaneous detection of antibodies bound to one or more cellular substrates and to one or more synthetic substrates, comprising the steps of:
   a) providing a mixture of cellular and synthetic substrates, wherein the synthetic substrate is a microparticle or bead coated with at least one of, purified native antigen and recombinant antigen to bind reactive antibodies, and wherein the cellular substrate is a mammalian cell or multiple mammalian cells obtained from organic tissue,
   b) incubating said mixture of substrates with a sample from a subject containing the antibody desired to be detected,
   c) detecting and identifying the antibodies bound to said substrates by fluorescent microscopy to obtain immunofluorescence image data and,
   d) evaluating the immunofluorescence image data obtained from the detection and identification step by using an automated pattern recognition interpretation system, wherein said immunofluorescence image data is evaluated according to the following hierarchy:
      a. determining a positive staining signal,
      b. identifying if cell substrate or synthetic substrate is stained,
      c. determining cellular substrate staining patterns of antibodies bound to said mammalian cell(s), wherein said cellular substrate staining patterns are selected from the group consisting of dsDNA staining, nuclear staining, perinuclear staining, chromatin of mitotic cells staining and cytoplasmic staining.

2. The method according to claim 1, wherein the cellular substrates are one or more from the group consisting of HEp-2 cells, human granulocytes and organic tissue.

3. The method according to claim 1, wherein at least one of an optical, fluorescent or physical characteristics of the substrates are used to identify said substrates.

4. The method according to claim 3, wherein the fluorescent characteristic of fluorophore concentration and the physical characteristic of size is used to identify the synthetic substrate.

5. The method according to claim 1, wherein the fluorescence microscopy used is multi-color microscopy to identify said at least one of, substrates and bound antibodies.

6. The method according to claim 1, further comprising labelling the cellular substrates with a fluorescent dye with blue emission, labelling the synthetic substrate with a fluorescent dye with green emission, while the specifically bound antibody which is detected by an anti-human immunoglobulin-specific antibody is labeled with a fluorescent dye with red emission.

7. The method according to claim 1, wherein the antibodies to be detected are anti-nuclear antibodies (ANA) or anti-neutrophil cytoplasmic antibodies (ANCA).

8. The method according to claim 7, wherein HEp-2 cells are used to analyse staining of anti-nuclear antibodies (ANA).

9. The method according to claim 7, wherein human granulocytes are used to analyse staining of anti-neutrophil cytoplasmic antibodies (ANCA).

10. The method according to claim 1, wherein the sample comprises blood, serum, cerebrospinal fluid, synovial fluid, or saliva obtained from a subject.

11. The method according to claim 1, wherein the interpretation system is controlled by specially designed software, consisting of modules for controlling devices and autofocus control, image acquisition, image analysis, and pattern recognition algorithms.

12. The method according to claim 1, wherein identification of staining patterns into cellular or synthetic and determination of cellular patterns is realized through a combination of structure and texture characteristics of the immunofluorescence image by defining a set of rules for each pattern.

13. A system for the simultaneous detection of antibodies bound to one or more cellular substrates and one or more synthetic substrates according to the method of claim 1, comprising,
   a) a fluorescent microscope with a camera, a motorized scanning stage and multichannel light-emitting diodes (LED), and
   b) a computing device with software consisting of modules for devices and autofocus control, automated image acquisition, automated image analysis, and automated pattern recognition algorithms whereby three colour channels are analysed.

14. A kit for the simultaneous detection of antibodies bound to one or more cellular substrates and to one or more synthetic substrates to the method of claim 1, comprising
   a) slides with fixed cellular substrate mixed with the antigen-coated synthetic substrate, wherein the cellular substrate is HEp-2 cells or human granulocytes, and the synthetic substrates are distinguished from one another according to their optical, fluorescent, or physical characteristics, and
   b) conjugate with immunoglobulin-specific antibody conjugated with a fluorescent label, preferably FITC, Cy5 and/or APC,
   and optionally,
   c) wash buffer, cover slips, covering medium, uncoated synthetic substrate, either with or without fluorescent label, and/or additional fluorescent labels for synthetic substrates.

15. The method according to claim 1, further comprising labelling the cellular substrates with DAPI, labelling the synthetic substrate with Rhodamine or FITC, while the specifically bound antibody which is detected by an anti-human immunoglobulin-specific antibody is labeled with Cy5 or APC.

16. The method of claim 1, wherein the microparticle size is between 1-100 μm.

17. The system of claim 13, wherein the three colour channels to be analyzed are blue, green and red.

* * * * *